(12) United States Patent
Varila

(10) Patent No.: US 10,004,580 B2
(45) Date of Patent: Jun. 26, 2018

(54) TOOTHBRUSH HEAD WITH A PORTION OF BRISTLES DISPOSED IN AN OUTWARD LEANING ANGLE

(71) Applicant: Reijo Varila, Helsinki (FI)

(72) Inventor: Reijo Varila, Helsinki (FI)

( * ) Notice: Subject to any disclaimer, the term of this patent is extended or adjusted under 35 U.S.C. 154(b) by 813 days.

(21) Appl. No.: 14/516,595

(22) Filed: Oct. 17, 2014

(65) Prior Publication Data

US 2015/0033488 A1 Feb. 5, 2015

Related U.S. Application Data

(63) Continuation-in-part of application No. 13/794,860, filed on Mar. 12, 2013, now Pat. No. 9,095,206.

(60) Provisional application No. 61/744,676, filed on Jun. 11, 2012.

(30) Foreign Application Priority Data

Nov. 26, 2012 (FI) ...................................... 20126243

(51) Int. Cl.
| | |
|---|---|
| *A46B 7/06* | (2006.01) |
| *A46B 13/02* | (2006.01) |
| *A61C 17/22* | (2006.01) |
| *A46B 9/04* | (2006.01) |
| *A46D 1/04* | (2006.01) |
| *A46B 9/02* | (2006.01) |
| *A46D 3/04* | (2006.01) |

(52) U.S. Cl.
CPC .............. *A61C 17/222* (2013.01); *A46B 7/06* (2013.01); *A46B 9/025* (2013.01); *A46B 9/026* (2013.01); *A46B 9/028* (2013.01); *A46B 9/04* (2013.01); *A46B 13/02* (2013.01); *A46D 1/04* (2013.01); *A46B 2200/1066* (2013.01); *A46D 3/04* (2013.01)

(58) Field of Classification Search
CPC ........ A46B 9/025; A46B 9/028; A61C 17/222
See application file for complete search history.

(56) References Cited

U.S. PATENT DOCUMENTS

| | | |
|---|---|---|
| D94,303 S | 1/1935 | Hadley |
| 4,619,009 A | 10/1986 | Rosenstatter |
| 5,467,495 A | 11/1995 | Boland et al. |
| D483,183 S | 12/2003 | De Salvo |
| 6,751,823 B2 * | 6/2004 | Biro ..................... A46B 13/008 15/22.1 |
| 6,892,413 B2 | 5/2005 | Blaustein et al. |
| D621,158 S | 8/2010 | Driesen et al. |
| 7,788,756 B2 | 9/2010 | Kraemer |
| 8,166,601 B2 | 5/2012 | Brown et al. |
| 2002/0138926 A1 | 10/2002 | Brown et al. |
| 2004/0034951 A1 | 2/2004 | Davies et al. |

(Continued)

*Primary Examiner* — Randall Chin
(74) *Attorney, Agent, or Firm* — Seppo Laine Oy

(57) ABSTRACT

The invention concerns a toothbrush head comprising a brush head housing, and a bristle carrier movable relative to the brush head housing around an axis of pivoting, the bristle carrier containing a plurality of tooth cleaning elements, wherein a first portion of bristles is arranged annularly and disposed in an outward leaning angle compared to the axis of pivoting by means of a wedge ring, and a second portion of bristles is arranged radially inwards of the first portion of bristles. The invention also concerns a method for manufacturing a toothbrush head.

15 Claims, 11 Drawing Sheets

(56) References Cited

U.S. PATENT DOCUMENTS

2005/0166343 A1 8/2005 Gavney
2006/0248667 A1 11/2006 Kraemer

* cited by examiner

TOOTHBRUSH HEAD WITH A PORTION OF BRISTLES DISPOSED IN AN OUTWARD LEANING ANGLE

RELATED APPLICATIONS

This application is a Continuation-in-Part of U.S. patent application Ser. No. 13/794,860, filed on Mar. 12, 2013, now U.S. Pat. No. 9,095,206, which claims priority to U.S. Provisional Application Ser. No. 61/744,676, filed on Jun. 11, 2012. The subject matter of which are incorporated by reference in their entirety.

TECHNICAL FIELD OF THE INVENTION

The present invention generally relates to replacement brush heads, for example for use with an electromagnetic assembly. The invention in particular relates to a toothbrush head with a portion of bristles disposed in an outward leaning angle. Additionally, methods of manufacture of the same are described herein.

BACKGROUND OF THE INVENTION

Plaque is the cause to gingivitis and other gum diseases. It is a sticky material made of bacteria, mucus, and food debris and deposits particularly in the gingival crevice and periodontal pockets evolved between the gum and teeth. Being concealed, technical level, conventional tooth brushes with right-angle bristles block rather than remove it when brushing the teeth. What is needed is a brush which is designed to remove plaque buildup at the neck of the tooth and the area between the teeth.

The document US 2013/0326833 A1 describes a replacement brush head for an electromagnetic driven toothbrush and a method of manufacturing such a brush head. The brush head includes a bristle carrier, where the bristle carrier has blind-end holes in which a plurality of tooth cleaning bristles can be fixedly attached. The bristles are arranged in inwardly centered rows, one behind the other. Bristles in outer rows are arranged in groups on both sides of the bristle carrier. Bristle groups are arranged with an outward leaning angle for efficient cleaning of the tooth neck area and gum pockets. Bristles in the inner rows can be shorter than the ones in the outer rows.

SUMMARY OF THE INVENTION

It is an object of certain embodiments of the present invention to provide a toothbrush head, in particular, a toothbrush head for use as a replaceable toothbrush head of an electric toothbrush system. It is further an object of certain embodiments of the present invention to provide a toothbrush head, wherein the brushing efficiency of the teeth neck areas, periodontal pockets and/or gums can be improved. Another object of certain embodiments of the present invention is to provide a toothbrush head, wherein bristles are arranged and orientated to improve holding and/or handling the toothbrush system during penetration of the interdental area. Additionally, it is an object of certain embodiment of the present invention to provide a method for manufacturing a toothbrush head.

It is an aspect of the present invention to provide a toothbrush head comprising a brush head housing coupled to a brush head shaft, a movable bristle carrier coupled to a pivoting axle of the brush head housing, and a mechanical linkage assembly coupled to the pivoting axle.

These and other objects are achieved by the embodiments of the present invention, as hereinafter described and claimed. According to an aspect of the invention, there is provided a toothbrush head, comprising a brush head housing, and a bristle carrier movable relative to the brush head housing around an axis of pivoting, the bristle carrier containing a plurality of tooth cleaning elements, wherein a first portion of bristles is arranged annularly and disposed in an outward leaning angle compared to the axis of pivoting by means of a wedge ring, and a second portion of bristles is arranged radially inwards of the first portion of bristles.

According to an embodiment, the wedge ring comprises a conically curved surface area.

According to another embodiment, the conically curved surface area is configured to bend the bristles of the first portion of bristles such that an outward leaning angle of the bristles of the first portion of bristles decreases radially outwards of the wedge ring.

In an embodiment, the wedge ring is an integral part of the bristle carrier. In another embodiment, the wedge ring is fixedly attached on a surface of the bristle carrier.

According to an embodiment, the second portion of the bristles is arranged radially inwards of the wedge ring.

According to another embodiment, the bristles of the first portion of bristles are longer than the bristles of the second portion of bristles.

In an embodiment, the wedge ring is configured to bend the first portion of bristles into an outward leaning angle in the range between 1° and 45°.

According to another aspect of the invention, the object of the embodiments can be also achieved by a method for manufacturing a toothbrush head, the method comprising the steps of:

attaching a first portion of bristles to a bristle carrier such that the first portion of bristles is orientated essentially parallel to an axis of pivoting, and attaching a second portion of bristles to the bristle carrier such that the second portion of bristles is orientated essentially parallel to an axis of pivoting and arranged radially inwards of the first portion of bristles, taking a wedge ring, and attaching the wedge ring to the bristle carrier such that the first portion of bristles is bent radially outwards by means of the wedge ring.

In an embodiment, the wedge ring is glued or otherwise fixedly attached to the bristle carrier.

In another embodiment, the position of the wedge ring relative to the bristle carrier is adjusted by a mechanical gripper or a Bernoulli gripper.

According to an embodiment, the position of the wedge ring relative to the bristle carrier is measured with a measurement system. According to another embodiment, the position of the wedge ring relative to the bristle carrier is classified as "OK" or "not OK" according to defined tolerance values by means of computer implemented instructions stored on a computer readable medium.

According to another aspect of the invention, the object of the embodiments can be also achieved by a toothbrush head, comprising a brush head housing, a bristle carrier movable relative to the brush head housing around an axis of pivoting, the bristle carrier comprising a conically curved surface area configured to bend a first portion of bristles radially outwards, a bristle carrier ring including the first portion of bristles and configured to be attached to the bristle carrier such that the first portion of bristles is bent radially outwards by means of the conically curved surface area, and a second portion of bristles arranged radially inwards of the first portion of bristles.

In an embodiment, the first portion of bristles is attached annularly to the bristle carrier ring.

In another embodiment, the bristle carrier comprises a wedge ring which includes the conically curved surface area. The wedge ring may be an integral part of the bristle carrier or fixedly attached to the bristle carrier.

According to an embodiment, the second portion of bristles is arranged radially inwards of the wedge ring.

According to another embodiment, the bristle carrier comprises an adjuster configured to adjust a position of the bristle carrier ring relative to the bristle carrier. In an embodiment, the bristle carrier comprises an adjuster configured to adjust an outward leaning angle of the bristles of the first portion of bristles and a length difference between the first and second portion of bristles.

Considerable advantages are obtained by means of the embodiments of the present invention. A toothbrush head for use as a replaceable toothbrush head of an electric toothbrush system is provided by means of the embodiments. Further, a toothbrush head is provided, wherein the brushing efficiency of the gingival crevice and teeth neck areas, periodontal pockets and/or gums is improved. Furthermore, a toothbrush head is provided, wherein bristle tufts are arranged and orientated to improve penetration of the interdental areas. Additionally, a toothbrush head is provided, wherein bristle tufts are arranged and orientated to improve holding and/or handling the toothbrush system during penetration of the interdental gum crevice.

There is also provided a method for manufacturing a toothbrush head. The manufacturing method is simple and allows high design flexibility. Bristles can be simultaneously or step-wise attached to the bristle carrier essentially perpendicular to the surface of the bristle carrier. Existing bristle setting equipment for setting the bristles can be therefore used. Attaching inclined bristles to the bristle carrier in order to obtain a toothbrush head with a portion of bristles disposed in an outward leaning angle is not required. By attaching the wedge ring to the bristle carrier the respective portion of bristles is simultaneously bent radially outwards into the predetermined position. The manufacturing method reduces manufacturing time and costs.

According to certain advantageous embodiments of the present invention, all bristles are fixed on a bristle carrier. The first portion of bristles is arranged annularly in the outermost row(s) and the second portion of the bristles is arranged radially inwards of the first portion of bristles. A separate wedge ring is pressed and fixed in position in-between the first portion of bristles and the second portion of bristle after setting the bristles. The bristles of the first portion of bristles are bent radially outwards to defined angle(s) by means of the wedge ring. Since the outward leaning angles of the bristles of the first portion of bristles decrease in a direction radially outwards, a relatively sharp peripheral tip of the bristles is formed. This relatively sharp peripheral tip especially improves the brushing efficiency of the gingival crevice and teeth neck areas, periodontal pockets and/or gums.

According to certain other advantageous embodiments of the present invention, the first portion of bristles is attached to a separate bristle carrier ring and the second portion of bristles is attached to the bristle carrier. The bristle carrier is provided with a wedge ring. The bristles of the first portion of bristles are bent radially outwards to defined angle(s) by means of the wedge ring at the stage of joining the bristle carrier ring and the bristle carrier. Since the outward leaning angles of the bristles of the first portion of bristles decrease in a direction radially outwards, a relatively sharp peripheral tip of the bristles is formed. This relatively sharp peripheral tip especially improves the brushing efficiency of the gingival crevice and teeth neck areas, periodontal pockets and/or gums. According to certain embodiments an additional adjuster is provided. In this case, the bristle length difference between the bristles of the first portion of bristles and the bristles of the second portion of bristles as well as the outward leaning angles of the bristles of the first portion of bristles can be adjusted by the user.

BRIEF DESCRIPTION OF THE DRAWINGS

For a more complete understanding of particular embodiments of the present invention and their advantages, reference is now made to the following descriptions, taken in conjunction with the accompanying drawings. In the drawings.

DETAILED DESCRIPTION OF EMBODIMENTS OF THE INVENTION

Figure 1:
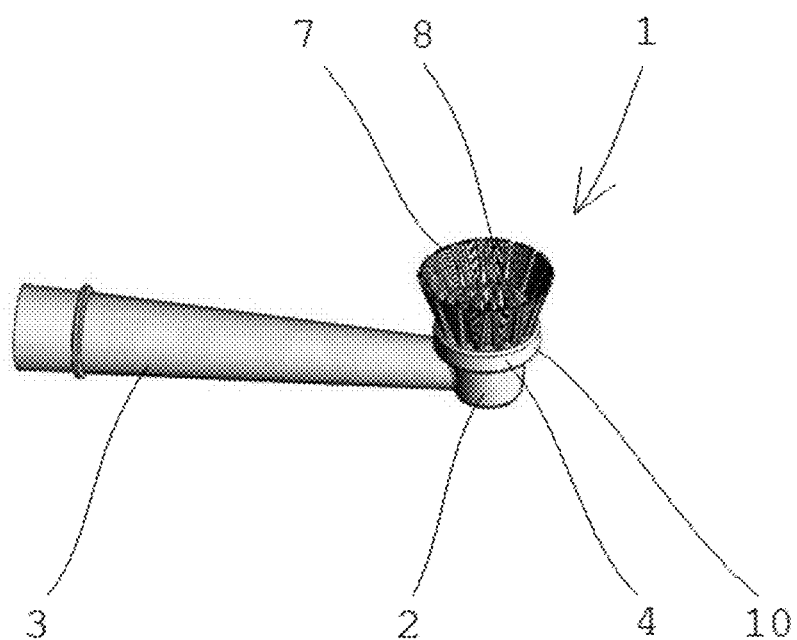
FIG. 1 illustrates a schematic perspective view of a toothbrush head according to an embodiment of the present invention.

The present invention generally relates to a replacement toothbrush head for electric toothbrushes. According to certain embodiments, the toothbrush head may comprise, or consist of, some or all of the following elements: a driving electromagnet assembled in a toothbrush head 1, a brush head shaft 3, a brush head housing 2 comprising a bottom portion with a pivoting axle 18 in the centre and a movable bristle carrier 4 for carrying tooth cleaning bristles, a moveable bristle carrier 4 connected and/or coupled to the central pivoting axle, a brush head bottom member fixedly connected to and/or coupled to a brush head shaft 3 and said brush head shaft 3 fixedly connected and/or coupled to said brush head housing 2, a brush head shaft 3 including a mechanical linkage assembly 6, a mechanical linkage assembly 6 connected to the movable bristle carrier 4 and an electromagnetic drive such that the bristle carrier 4 can pivot around a brush head pivoting axis 5 when the electromagnet is actuated.

The bristle carrier 4 can have blind-end bores in which a plurality of tooth cleaning bristles or other tooth cleaning elements can be fixedly attached. A first portion of bristles 7 and a second portion of bristles 8 are fixedly attached in the respective blind-end bores. The bristles and/or other tooth cleaning elements of the first portion of bristles 7 can be arranged into bristle tufts and the bristles and/or other tooth cleaning elements of the second portion of bristles 8 can be arranged into bristle tufts. Each of the bristle tufts contains a plurality of the bristles or other tooth cleaning elements. The bristles or other tooth cleaning elements are attached to the bristle carrier for example either by using a metal plate anchor as known per se, by the same plastic material used for injection molding of the bristle carrier or by any other method known by the art.

The bristle carrier 4 is configured to pivot around an axis of pivoting 5. The pivoting angle is typically in the range between +90° and −90°, normally in the range between +45° and −45°, for example in the range between +20° and −20° from stationary rest position. According to certain other embodiments, the bristle carrier 4 is configured to rotate around an axis of rotation.

In FIG. 1 a schematic perspective view of a toothbrush head 1 according to an embodiment of the present invention is illustrated. The toothbrush head 1 comprises a brush head housing 2, a brush head shaft 3 and a moveable bristle carrier 4. The moveable bristle carrier 4 has an outer contour 10 which is shown as a circle. The outer contour 10 of the bristle carrier may also be, for example, elliptical or any other desired symmetric or asymmetric shape according to certain embodiments. The brush head housing 2 may be an integral portion of the brush head shaft or separately connected to the brush head shaft in a manufacturing process.

A first portion of bristles 7 is arranged annularly and disposed in an outward leaning angle compared to an axis of pivoting 5, which axis is not shown in FIG. 1, and a second portion of bristles 8 is arranged radially inwards of the first portion of bristles 7. The outward leaning angle is typically in the range between 45° and 1°, normally in the range between 30° and 1°, preferably in the range between 25° and 15°, for example 18°. The outward leaning angle of the bristles of the first portion of bristles can vary so that some of the bristles have a more pronounced outward leaning angle than others. The second portion of bristles 8 is orientated essentially perpendicular to a surface of the bristle carrier 4. In other words, the bristles of the second portion of bristles 8 are arranged essentially parallel to the axis of pivoting 5. The bristles of the first portion of bristles 7 form a plurality of respective bristle tufts. Also the bristles of the second portion of bristles 8 form a plurality of respective bristle tufts. The bristles of the first portion of bristles 7 are longer than the bristles of the second portion of bristles 8. The length difference 20 between the tips of the bristles of the first portion of bristles 7 and the tips of the bristles of the second portion of bristles 8 is typically in the range between 0% and 60% of the length of the bristles of the second portion of bristles 8, preferably in the range between 10% and 50% of the length of the bristles of the second portion of bristles 8, for example 45% of the length of the bristles of the second portion of bristles 8. The bristles of the first portion of bristles 7 can be longer than the bristles of the second portion of bristles 8, preferably at least 1.2× longer, even more preferably between 1.5× and 2.0× longer than the bristles of the second portion of bristles 8.

Figure 2:
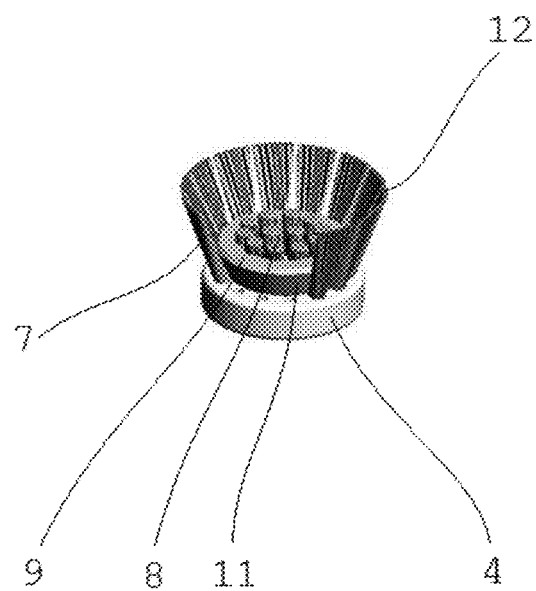
FIG. 2 illustrates a schematic view of a bristle carrier according to an embodiment of the present invention.

In FIG. 2 a schematic view of a bristle carrier 4 according to an embodiment of the present invention is illustrated. Some of the bristles of the first portion of bristles 7 are not shown in FIG. 2 in order to clearly illustrate a wedge ring 9. The wedge ring 9 is fixedly attached on the surface of the bristle carrier. According to certain embodiments, the wedge ring 9 may be also an integral part of the bristle carrier 4. Typically the wedge ring 9 is made of the same material as the bristle carrier 4. A first portion of bristles 7 is further arranged annularly and disposed in an outward leaning angle compared to the axis of pivoting 5, which is not shown in FIG. 2, by means of the wedge ring 9. The outward leaning angle is typically in the range between 0° and 45°, preferably between 5° and 40°, for example 25°. A second portion of bristles 8 is arranged radially inwards of the first portion of bristles 7. The second portion of the bristles 8 is further arranged radially inwards of the wedge ring 9. The wedge ring 9 comprises a conically curved surface area 11. According to certain other embodiments, the wedge ring 9 comprises a cross section in the form of a triangle, square or circle or any other geometrical shape by means of which the bristles of the first portion of bristles 7 can be bent radially outwards.

According to a certain embodiment, the conically curved surface area 11 of the wedge ring 9 is configured to bend the bristles of the first portion of bristles 7 such that the outward leaning angle of the bristles of the first portion of bristles 7 decreases radially outwards of the wedge ring 9. In other words, the outward leaning angle of the bristles of the first portion of bristles which are directly in contact with the conically curved surface area 11 of the wedge ring 9 is greater than the outward leaning angle of the bristles of the first portion of bristles which are arranged in the outermost row. Therefore, the first portion of bristles 7 forms an annular peripheral tip 12 above the bristle carrier 4 which tip 12 can be considered to be relatively sharp. The peripheral tip 12 advantageously improves the brushing efficiency of the gingival crevice, teeth neck areas and evolving periodontal pockets and/or gums.

Figure 3:
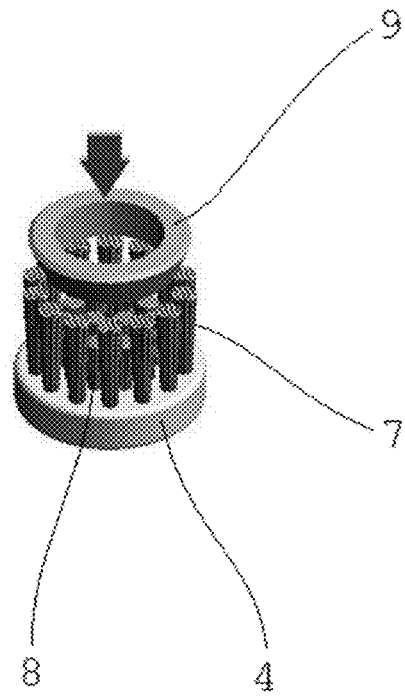
FIG. 3 illustrates a schematic perspective view of a bristle carrier according to an embodiment of the present invention during a manufacturing process before attachment of a wedge ring.

In FIG. 3 a schematic perspective view of a bristle carrier according to an embodiment of the present invention during a manufacturing process before attachment of a wedge ring is illustrated. The first portion of bristles 7 is fixedly attached in blind-end bores of a bristle carrier 4 in such a way that the first portion of bristles 7 is orientated essentially parallel to an axis of pivoting 5, which is not shown in FIG. 3. Also a second portion of bristles 8, which is arranged radially inwards of the first portion of bristles 7, is fixedly attached in blind-end bores of the bristle carrier 4 in such a way that the second portion of bristles 8 is orientated essentially parallel to the axis of pivoting 5. Then, taking of a wedge ring 9 takes place, for example, by means of a mechanical gripper or a Bernoulli gripper and the wedge ring 9 is moved relative to the bristle carrier. At a later stage, which is not shown in FIG. 3, the wedge ring 9 is fixedly attached to the bristle carrier 4 such that the first portion of bristles 7 is bent radially outwards by means of the wedge ring 9.

Figure 4:
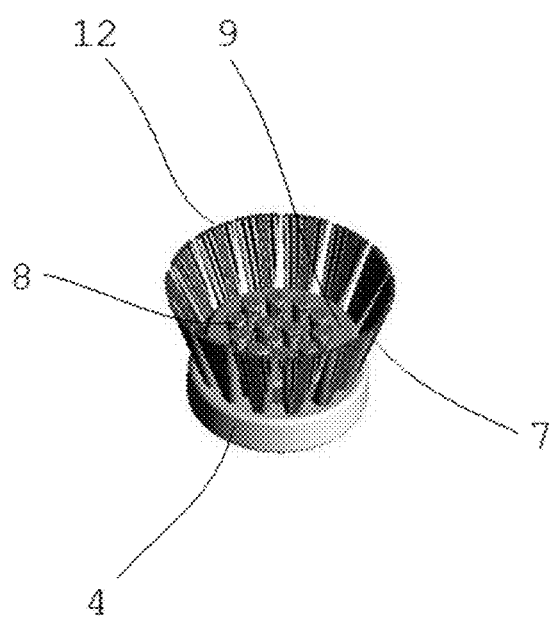
FIG. 4 illustrates a schematic perspective view of a bristle carrier according to an embodiment of the present invention after attachment of a wedge ring.

In FIG. 4 a schematic perspective view of a bristle carrier 4 according to an embodiment of the present invention after attachment of a wedge ring 9 on the surface of the bristle carrier 4 is illustrated. The wedge ring 9 deforms the bristles of the first portion of bristles 7 into a predetermined orientation. The bristles of the second portion of bristles 8 remain essentially in their orientation.

Figure 5:
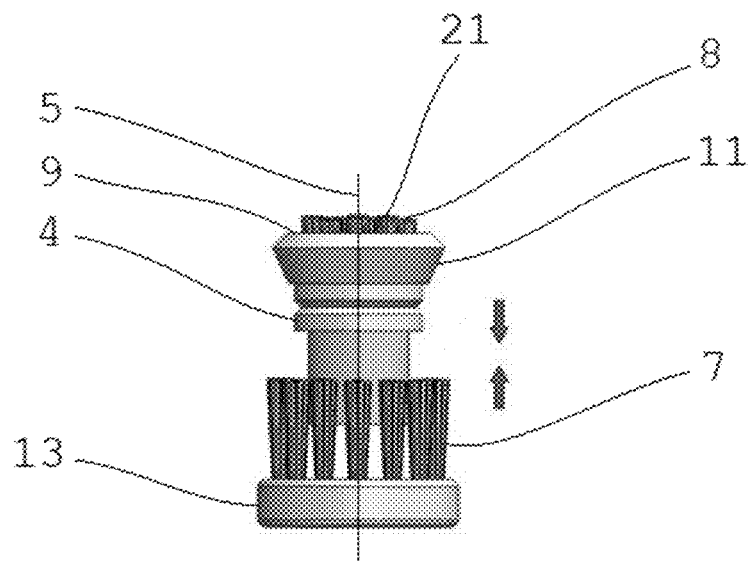
FIG. 5 illustrates a schematic side view of a toothbrush head according to an embodiment of the present invention during manufacturing.

In FIG. 5 a schematic side view of a toothbrush head 1 according to an embodiment of the present invention during manufacturing is illustrated. The toothbrush head 1 comprises a brush head housing 2, which is not shown in FIG. 5, and a bristle carrier 4 movable relative to the brush head housing 2 around an axis of pivoting 5. The bristle carrier 4 comprises a conically curved surface area 11 configured to bend a first portion of bristles 7 radially outwards. The toothbrush head 1 further comprises a bristle carrier ring 13 including the first portion of bristles 7 and configured to be attached to the bristle carrier 4 such that the first portion of bristles 7 is bent radially outwards by means of the conically curved surface area 11. A second portion of bristles 8 is arranged radially inwards of the first portion of bristles 7. The bristles of the first portion of bristles 7 and the bristles of the second portion of bristles 8 are orientated essentially parallel to the axis of pivoting 5. The top surface 21 formed by the bristles of the second portion of bristles 8 may be conical according to certain embodiments in order to face tooth curvature sufficiently. The first portion of bristles 7 is arranged annularly in blind-end bores of the bristle carrier ring 13 and the second portion of bristles 8 is arranged in blind-end bores of the bristle carrier 4. In FIG. 5 the bristle carrier 4 and the bristle carrier ring 13 are shown separated from each other. During manufacturing of the toothbrush head the bristle carrier 4 and the bristle carrier ring 13 are moved relative to each other in order to attach the separate bristle carrier ring 13 to the bristle carrier 4. The bristle carrier 4 comprises a wedge ring 9 which includes the conically curved surface area 11. The wedge ring 11 may be an integral part of the bristle carrier 4 or may be a separate part which is fixedly attached to the bristle carrier 4. Typically the wedge ring 9 is made in an injection molding process step together with the bristle carrier 4. The second portion of bristles 8 is arranged radially inwards of the wedge ring 11.

Figure 6:
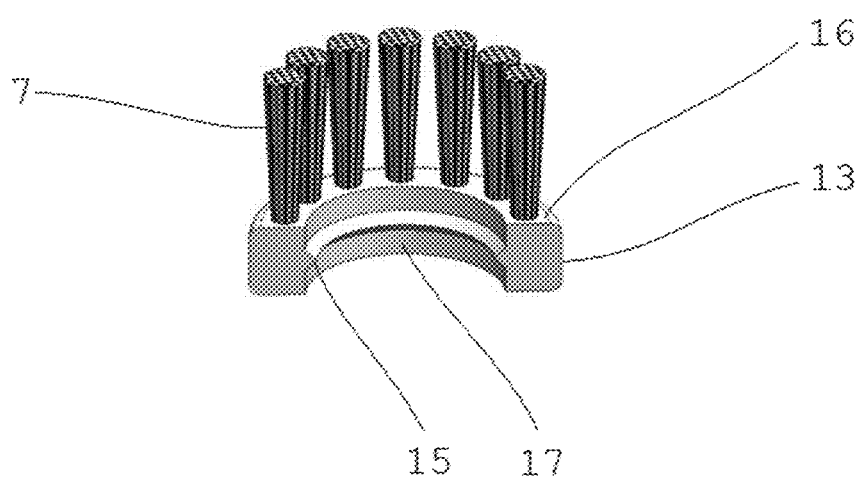
FIG. 6 illustrates a schematic cross-sectional view of a bristle carrier ring of a toothbrush head according to an embodiment of the present invention.

In FIG. 6 a schematic cross-sectional view of a separate bristle carrier ring 13 of a toothbrush head 1 according to an embodiment of the present invention is illustrated. The first portion of bristles 7 is arranged annularly in blind-end bores of the bristle carrier ring 13. The bristles of the first portion of bristles 7 form bristle tufts and are arranged essentially perpendicular to the mounting surface 16 of the bristle carrier ring 13. The bristle carrier ring 13 further comprises a tongue 15 on the inner surface area 17 of the bristle carrier ring 13, which tongue is configured to be attached to a groove 14 of a bristle carrier 4.

Figure 7:
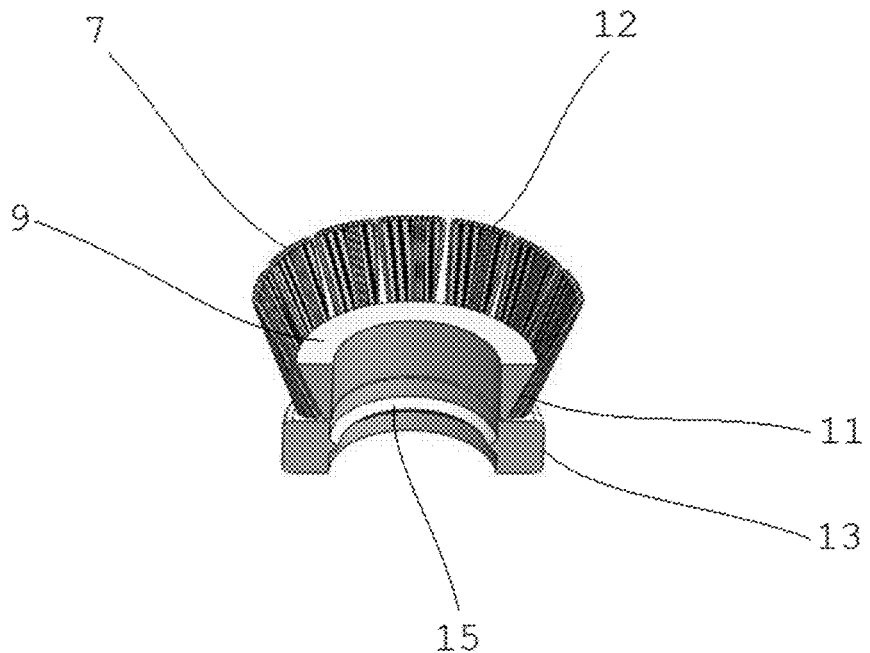
FIG. 7 illustrates a schematic cross-sectional view of a bristle carrier ring of a toothbrush head according to an embodiment of the present invention, wherein the first portion of bristles is bent radially outwards by means of a wedge ring.

In FIG. 7 a schematic cross-sectional view of a bristle carrier ring 13 of a toothbrush head 1 according to an embodiment of the present invention is illustrated, wherein the first portion of bristles 7 is bent radially outwards by means of a wedge ring 13. The wedge ring 13 bends the bristles of the first portion of bristles 7 radially outwards. The conically curved surface area 11 of the wedge ring 13 is configured to bend the bristles of the first portion of bristles 7 such that the outward leaning angle of the bristles of the first portion of bristles 7 decreases radially outwards of the wedge ring 13. In other words, the cross sectional area of the bristle tufts of the first portion of bristles 7 changes along the length of the bristle tufts. A thinned sharp ended shape of the tips of the bristle tufts of the first portion of bristles 7 is created. The bristle tufts of the first portion of bristles 7 form a relatively sharp peripheral tip 12 which can be advantageously used for brushing the teeth neck areas, gingival crevice and evolved periodontal pockets, for instance. The relatively sharp peripheral tip also enables cleaning the interdental areas. Additionally the stiffness of the peripheral tip 12 is increased which improves lifetime of the bristles of the first portion of bristles 7.

Figure 8:
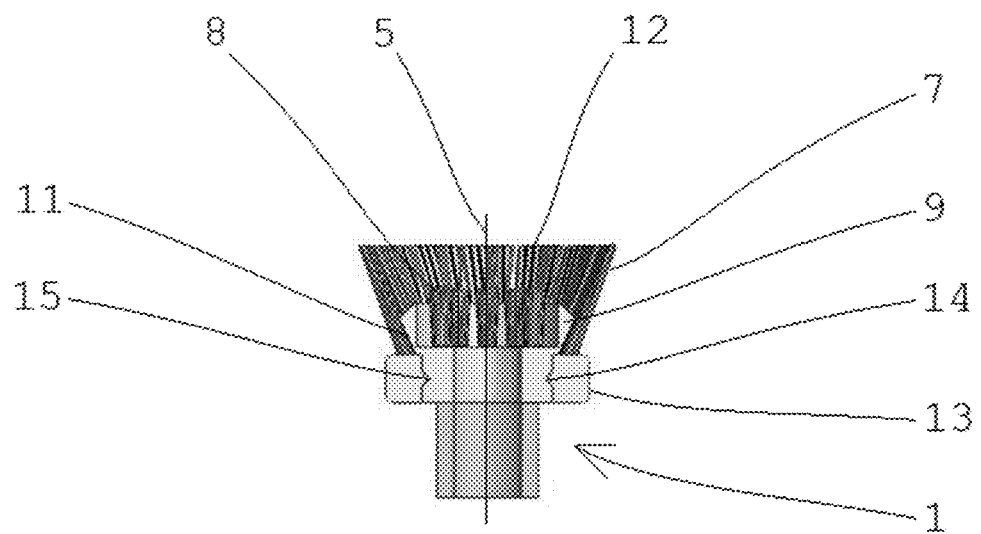
FIG. 8 illustrates a schematic cross-sectional view of a bristle carrier ring mounted to a bristle carrier of a toothbrush head according to an embodiment of the present invention.

In FIG. 8 a schematic cross-sectional view of a bristle carrier ring 13 mounted to a bristle carrier 4 of a toothbrush head 1 according to an embodiment of the present invention is illustrated. The separate bristle carrier ring 13 is pressed into its final position such that the position of the tongue 15 coincides with the position of the groove 14 of the bristle carrier 4. The wedge ring 13 of the bristle carrier 4 comprises a conically curved surface area 11 configured to bend the first portion of bristles 7 radially outwards. The second portion of bristles 8 is arranged radially inwards of the wedge ring 13.

Figure 9A:
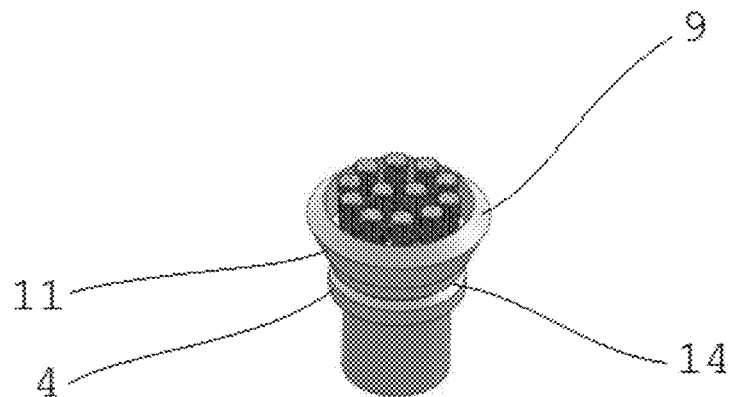
FIG. 9a illustrates a schematic perspective view of a bristle carrier of a toothbrush head according to an embodiment of the present invention.

In FIG. 9a a schematic perspective view of a bristle carrier 4 of a toothbrush head 1 according to an embodiment of the present invention is illustrated. Ordinary filament type bristles form the bristle tufts of the second portion of bristles 8 radially inwards of the wedge ring 9. The bristles of the second portion of bristles 8 typically have a round cross-sectional shape.

Figure 9B:
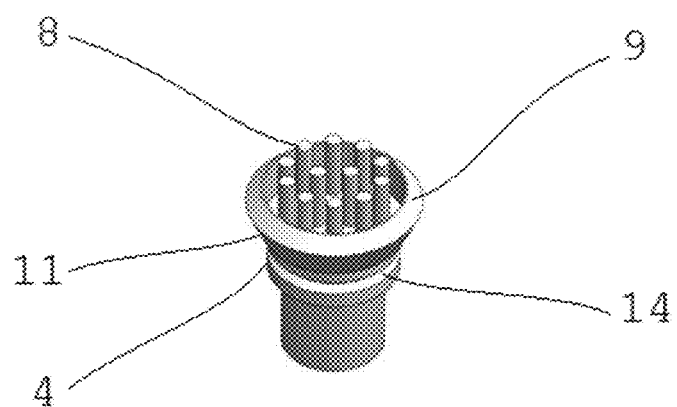
FIG. 9b illustrates a schematic perspective view of a bristle carrier of a toothbrush head according to an embodiment of the present invention.

In FIG. 9b a schematic perspective view of a bristle carrier 4 of a toothbrush head 1 according to an embodiment of the present invention is illustrated. Tooth cleaning elements 8 having an annular cross-sectional area are arranged radially inwards of the wedge ring 9.

Figure 9C:
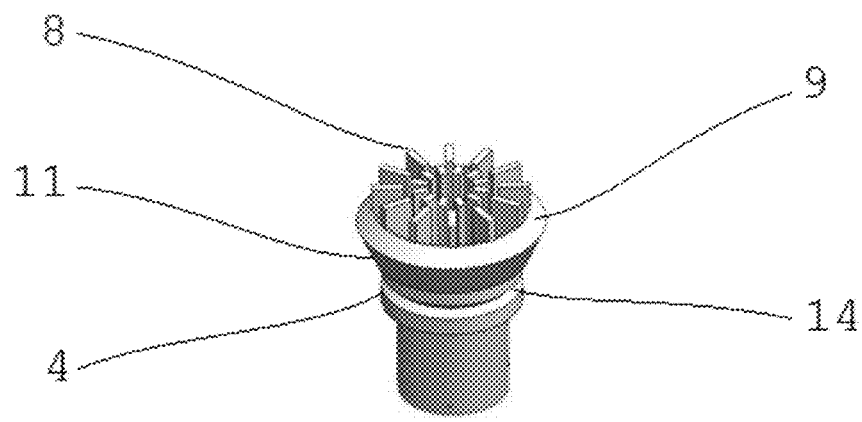
FIG. 9c illustrates a schematic perspective view of a bristle carrier of a toothbrush head according to an embodiment of the present invention.

In FIG. 9c a schematic perspective view of a bristle carrier 4 of a toothbrush head 1 according to an embodiment of the present invention is illustrated. Tooth cleaning elements 8 having a rectangular cross-sectional area are arranged radially inwards of the wedge ring 9.

Figure 10:
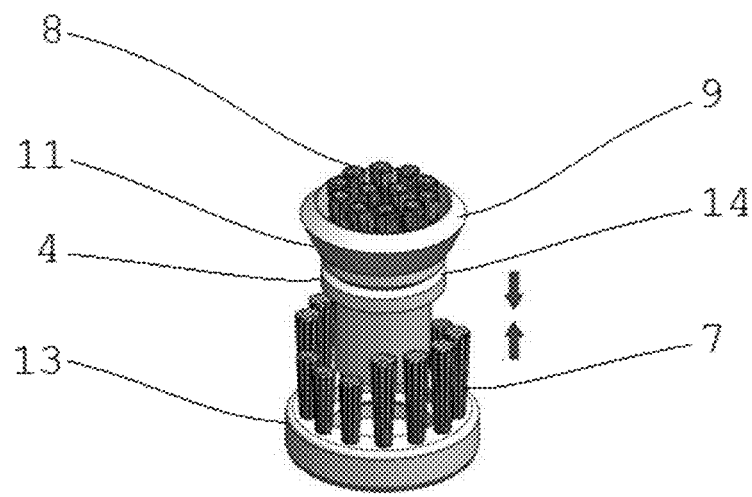
FIG. 10 illustrates a schematic perspective view of a toothbrush head according to an embodiment of the present invention during manufacturing.

In FIG. 10 a schematic perspective view of a toothbrush head 1 according to an embodiment of the present invention during manufacturing is illustrated. The bristles of the first portion of bristles 7 attached to the bristle carrier ring 13 form bristle tufts of different length. The bristles are attached to the bristle carrier ring 13 perpendicular to the mounting surface 16 regardless of size. Bristles of the second portion of bristles 8 attached to the bristle carrier 4 may have the same length or different lengths.

Figure 11:
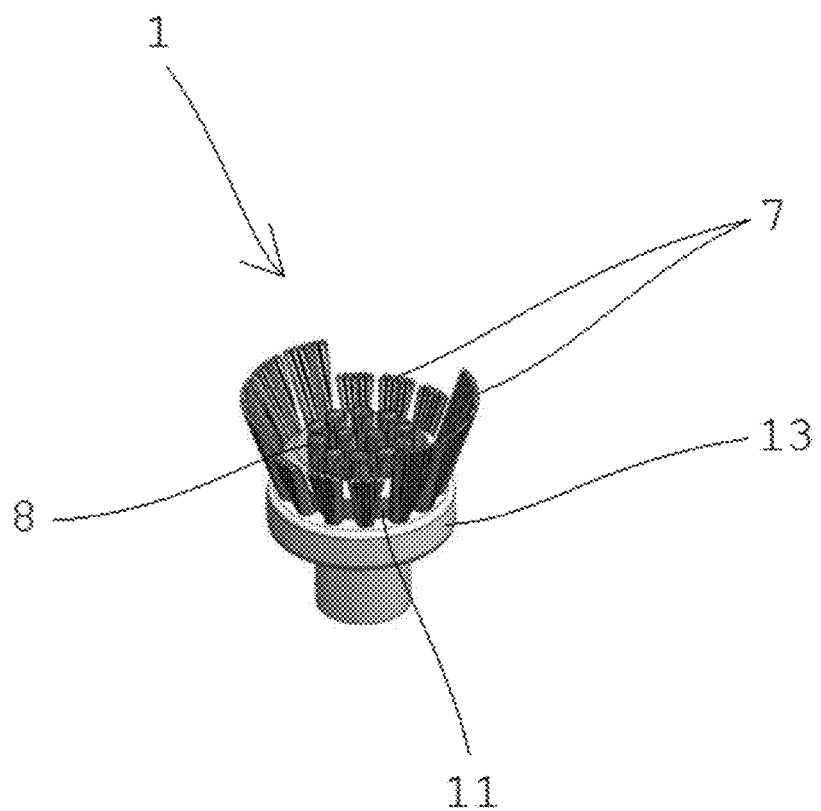
FIG. 11 illustrates a schematic perspective view of a bristle carrier ring mounted to a bristle carrier of a toothbrush head according to an embodiment of the present invention.

In FIG. 11 a schematic perspective view of a bristle carrier ring 13 mounted to a bristle carrier 4 of a toothbrush head 1 according to an embodiment of the present invention is illustrated. The separate bristle carrier ring 13 is pressed into its final position such that bristle tufts of different length are bent radially outwards. The bristles of the first portion of bristles 7 are bent radially outwards by means of the conically curved surface area 11 of the wedge ring 9 regardless of the length of the bristles.

Figure 12A:
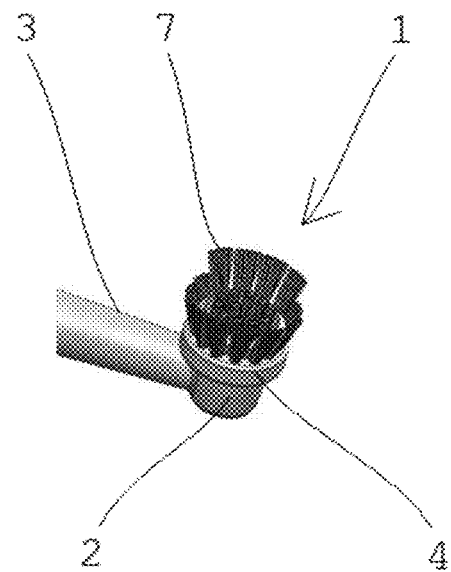
FIG. 12a illustrates a schematic perspective view of a toothbrush head according to an embodiment of the present invention.

In FIG. 12a a schematic perspective view of a toothbrush head 1 according to an embodiment of the invention is illustrated. The bristles of the first portion of bristles 7 are bent radially outwards by means of the conically curved surface area 11 of the wedge ring 9 regardless of the length of the bristles. The longer bristle tufts of the first portion of bristles 7 form two groups located on opposite sides of the longitudinal axis of the brush head shaft 3.

Figure 12B:
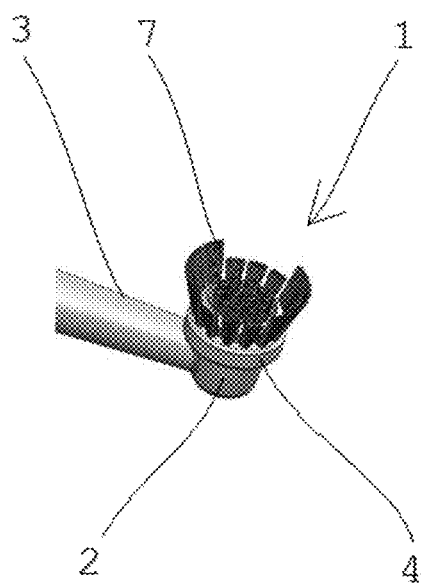
FIG. 12b illustrates a schematic perspective view of a toothbrush head according to an embodiment of the present invention.

In FIG. 12b a schematic perspective view of a toothbrush head according to an embodiment of the invention is illustrated. The bristles of the first portion of bristles 7 are bent radially outwards by means of the conically curved surface area 11 of the wedge ring 9 regardless of the length of the bristles. The longer bristle tufts of the first portion of bristles 7 form two groups extending over the longitudinal axis of the brush head shaft 3.

Figure 13A:
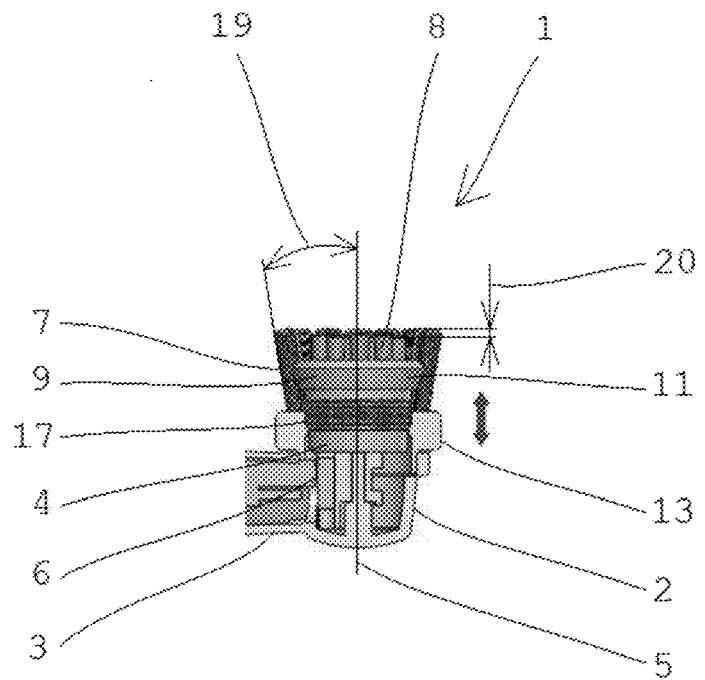
FIG. 13a illustrates a schematic cross sectional view of a toothbrush head according to an embodiment of the present invention.

In FIG. 13a a schematic cross sectional view of a toothbrush head 1 according to an embodiment of the invention is illustrated. The toothbrush head 1 comprises a brush head housing 2 and a bristle carrier 4 movable relative to the brush head housing 2 around an axis of pivoting 5. The bristle carrier 4 comprises a wedge ring 9 with a conically curved surface area 11 configured to bend a first portion of bristles 7 radially outwards. A bristle carrier ring 13 includes the first portion of bristles 7 and is attached to the bristle carrier 4. The first portion of bristles 7 is arranged annularly in blind-end bores of the bristle carrier ring 13. The bristle carrier 4 further comprises an adjuster 17 configured to adjust the position of the bristle carrier ring 13 relative to the bristle carrier 4 and to likewise adjust the outward leaning angle 19 of the bristles of the first portion of bristles 7. By means of the adjuster 17 it is possible to adjust the bristle length difference 20 between the bristles of the first portion of bristles 7 and the bristles of the second portion of bristles 8. The bristles of the second portion of bristles 8 are arranged radially inwards of the first portion of bristles 7 and the wedge ring 9.

Figure 13B:
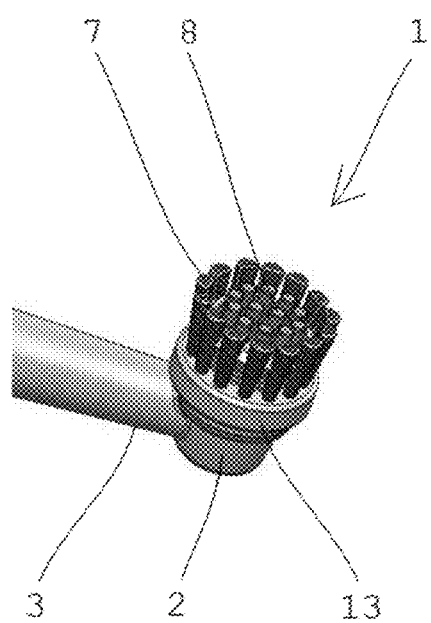
FIG. 13b illustrates a schematic perspective view of a toothbrush head according to the embodiment shown in FIG. 13a, FIG. 14a illustrates a schematic cross sectional view of a toothbrush head according to an embodiment of the present invention.

In FIG. 13b a schematic perspective view of a toothbrush head according to the embodiment shown in FIG. 13a is illustrated.

Figure 14A:
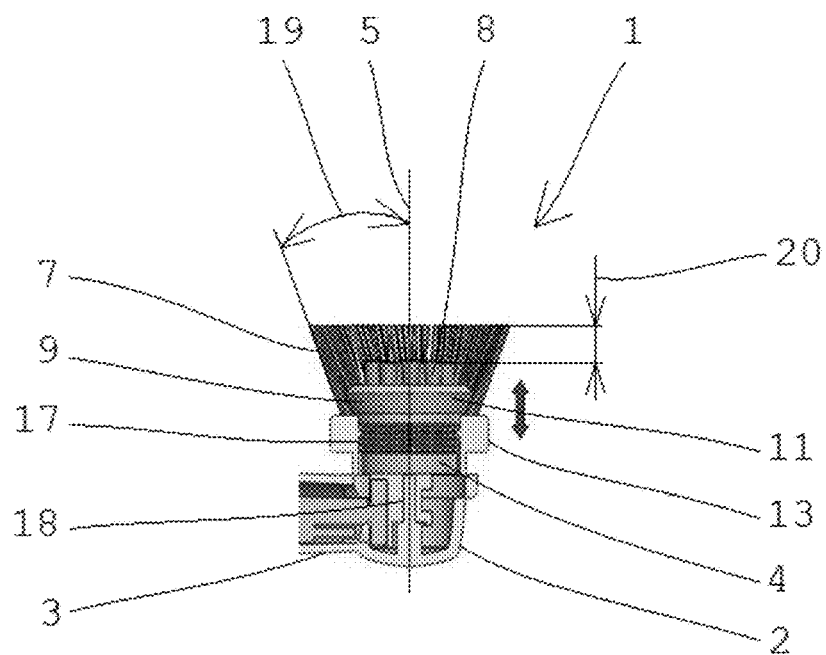
FIG. 14b illustrates a schematic perspective view of a toothbrush head according to the embodiment shown in FIG. 14a, and FIG. 15 illustrates a flow chart diagram of a method for manufacturing a toothbrush head according to certain embodiments of the present invention.

In FIG. 14a a schematic cross sectional view of a toothbrush head according to an embodiment of the invention is illustrated. The toothbrush head 1 comprises a brush head housing 2 and a bristle carrier 4 movable relative to the brush head housing 2 around an axis of pivoting 5. The bristle carrier 4 comprises a wedge ring 9 with a conically curved surface area 11 configured to bend a first portion of bristles 7 radially outwards. A bristle carrier ring 13 includes the first portion of bristles 7 and is attached to the bristle carrier 4. The first portion of bristles 7 is arranged annularly in blind-end bores of the bristle carrier ring 13. The bristle carrier 4 further comprises an adjuster 17 configured to adjust the position of the bristle carrier ring 13 relative to the bristle carrier 4 and to adjust the outward leaning angle 19 of the bristles of the first portion of bristles 7. Compared to the embodiment shown in FIG. 13a the bristle length difference 20 and likewise the outward leaning angle 19 of the bristles of the first portion of bristles 7 are increased. I.e., by means of the adjuster 17 it is also possible to adjust the outward leaning angle 19 of the bristles of the first portion of bristles 7.

Figure 14B:
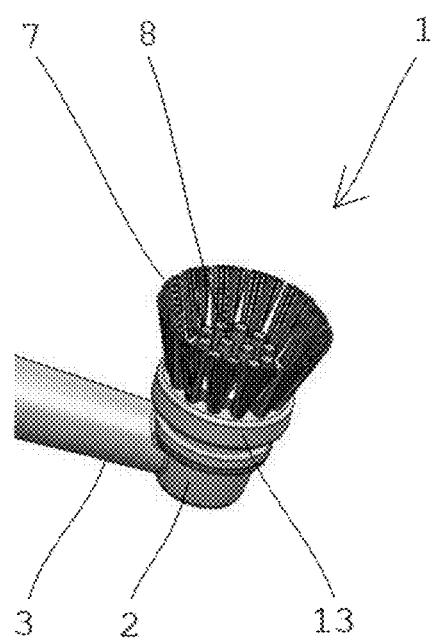

In FIG. 14b a schematic perspective view of a toothbrush head according to the embodiment shown in FIG. 14a is illustrated.

Figure 15:
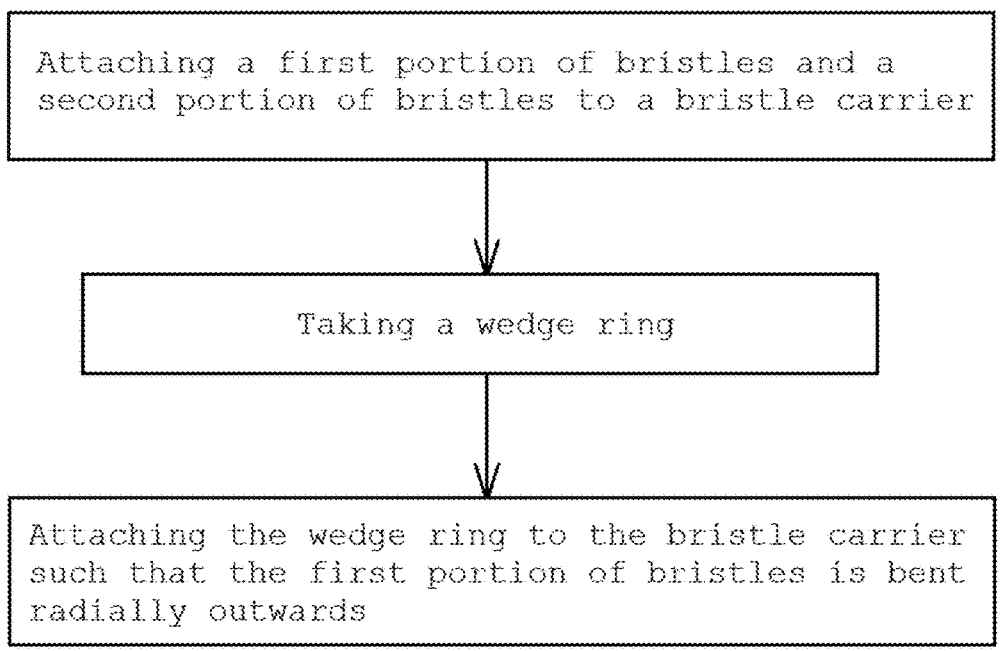

In FIG. 15 a flow chart diagram of a method for manufacturing a toothbrush head according to certain embodiments of the present invention is illustrated. A first portion of bristles is attached to a bristle carrier such that the first portion of bristles is orientated essentially parallel to an axis of pivoting and a second portion of bristles is attached to the bristle carrier such that the second portion of bristles is orientated essentially parallel to an axis of pivoting and arranged radially inwards of the first portion of bristles. Then taking of a wedge ring takes place, for example, by means of a mechanical gripper or a Bernoulli gripper and the wedge ring is moved relative to the bristle carrier. At a later stage the wedge ring 9 is fixedly attached to the bristle carrier such that the first portion of bristles is bent radially outwards by means of the wedge ring. The wedge ring may be fixedly attached to the bristle carrier by gluing or may be otherwise attached.

According to certain embodiments, the position of the wedge ring relative to the bristle carrier may be measured with a measurement system during the attachment of the wedge ring and/or after the attachment of the wedge ring. The position of the wedge ring may then be classified as "OK" or "not OK" according to defined tolerance values by means of computer implemented instructions stored on a computer readable medium.

Although the present invention has been described in detail for the purpose of illustration, various changes and modifications can be made within the scope of the claims. In addition, it is to be understood that the present disclosure contemplates that, to the extent possible, one or more features of any embodiment may be combined with one or more features of any other embodiment.

It is to be understood that the embodiments of the invention disclosed are not limited to the particular structures, process steps, or materials disclosed herein, but are extended to equivalents thereof as would be recognized by those ordinarily skilled in the relevant arts. It should also be understood that terminology employed herein is used for the purpose of describing particular embodiments only and is not intended to be limiting.

LIST OF REFERENCE NUMBERS

1 Toothbrush head
2 Brush head housing
3 Brush head shaft
4 Bristle carrier
5 Axis of pivoting
6 Mechanical linkage assembly
7 First portion of bristles
8 Second portion of bristles
9 Wedge ring
10 Outer contour of the bristle carrier
11 Conically curved surface area
12 Peripheral tip 13 Bristle carrier ring
14 Groove
15 Tongue
16 Mounting surface
17 Adjuster
18 Pivoting axle
19 Outward leaning angle
20 Bristle length difference
21 Top surface

The invention claimed is:

1. A toothbrush head, comprising;
a brush head housing, and
a bristle carrier movable relative to the brush head housing around an axis of pivoting, the bristle carrier containing a plurality of tooth cleaning elements, and
a wedge ring, wherein
a first portion of bristles is arranged annularly and disposed in an outward leaning angle compared to the axis of pivoting by the wedge ring, and
a second portion of bristles is arranged radially inwards of the first portion of bristles.

2. The toothbrush head according to claim 1, wherein the wedge ring comprises a conically curved surface area.

3. The toothbrush head according to claim 1, wherein a conically curved surface area is configured to bend the bristles of the first portion of bristles such that an outward leaning angle of the bristles of the first portion of bristles decreases radially outwards of the wedge ring.

4. The toothbrush head according to claim 1, wherein the wedge ring is an integral part of the bristle carrier.

5. The toothbrush head according to claim 1, wherein the wedge ring is fixedly attached on a surface of the bristle carrier.

6. The toothbrush head according to claim 1, wherein the second portion of the bristles is arranged radially inwards of the wedge ring.

7. The toothbrush head according to claim 1, wherein bristles of the first portion of bristles are longer than bristles of the second portion of bristles.

8. The toothbrush head according to claim 1, wherein the wedge ring is configured to bend the first portion of bristles into an outward leaning angle in the range between 1° and 45°.

9. A toothbrush head, comprising;
a brush head housing,
a bristle carrier movable relative to the brush head housing around an axis of pivoting, the bristle carrier comprising a conically curved surface area configured to bend a first portion of bristles radially outwards,
a bristle carrier ring including the first portion of bristles and configured to be attached to the bristle carrier such that the first portion of bristles is bent radially outwards by the conically curved surface area, and
a second portion of bristles arranged radially inwards of the first portion of bristles.

10. The toothbrush head according to claim 9, wherein the first portion of bristles is attached annularly to the bristle carrier ring.

11. The toothbrush head according to claim 9, wherein the bristle carrier comprises a wedge ring which includes the conically curved surface area.

12. The toothbrush head according to claim 9, wherein the second portion of bristles is arranged radially inwards of the wedge ring.

13. The toothbrush head according to claim 9, wherein the bristle carrier comprises an adjuster configured to adjust a position of the bristle carrier ring relative to the bristle carrier.

14. The toothbrush head according to claim 9, wherein the bristle carrier comprises an adjuster configured to adjust an outward leaning angle of the bristles of the first portion of bristles and a length difference between the first and second portion of bristles.

15. The toothbrush head according to claim 9, wherein the conically curved surface area is configured to bend the bristles of the first portion of bristles such that an outward leaning angle of the bristles of the first portion of bristles decreases radially outwards of the wedge ring.

* * * * *